(12) United States Patent
Samudre (10) Patent No.: US 11,707,403 B1
(45) Date of Patent: Jul. 25, 2023

(54) SYSTEMS AND METHODS FOR TREATMENT OF ABNORMAL VISUAL DEVELOPMENT

(71) Applicant: Sandeep Samudre, Chesapeake, VA (US)

(72) Inventor: Sandeep Samudre, Chesapeake, VA (US)

(*) Notice: Subject to any disclaimer, the term of this patent is extended or adjusted under 35 U.S.C. 154(b) by 1,011 days.

(21) Appl. No.: 16/120,597

(22) Filed: Sep. 4, 2018

Related U.S. Application Data (60) Provisional application No. 62/553,865, filed on Sep. 3, 2017.

(51) Int. Cl.
*A61H 5/00* (2006.01)
*G16H 20/40* (2018.01)
*G06T 11/00* (2006.01)

(52) U.S. Cl.
CPC .............. *A61H 5/005* (2013.01); *G16H 20/40* (2018.01); *A61H 2201/5007* (2013.01); *A61H 2201/5043* (2013.01); *A61H 2201/5092* (2013.01); *G06T 11/00* (2013.01)

(58) Field of Classification Search
CPC .............. A61H 5/005; G16H 20/40; A61H 2201/5007; A61H 2201/5043; A61H 2201/5092; G06T 11/00
See application file for complete search history.

(56) References Cited

U.S. PATENT DOCUMENTS

| | | | |
|---|---|---|---|
| 5,956,126 A | 9/1999 | Cody | |
| 6,511,175 B2 | 1/2003 | Hay et al. | |
| 6,912,301 B1 | 6/2005 | Lin et al. | |
| 7,033,025 B2 | 4/2006 | Winterbotham | |
| 7,452,067 B2 | 11/2008 | Gross | |
| 7,828,434 B2 | 11/2010 | Coulter et al. | |
| 8,485,661 B2 | 7/2013 | Yoo et al. | |
| 8,542,326 B2 | 9/2013 | Macnaughton et al. | |
| D692,941 S | 11/2013 | Klinar et al. | |
| 8,622,544 B2 | 1/2014 | Brown et al. | |
| 8,624,965 B2 | 1/2014 | Park et al. | |
| 8,708,484 B2 | 4/2014 | Reichow et al. | |
| D711,959 S | 8/2014 | Javh et al. | |
| RE45,394 E | 3/2015 | Carlow et al. | |

(Continued)

FOREIGN PATENT DOCUMENTS

| | | | |
|---|---|---|---|
| CN | 102600032 A | 7/2012 | |
| CN | 103857370 A | 6/2014 | |
| EP | 2428836 A1 | 3/2012 | |
| EP | 2479600 A1 | 7/2012 | |

(Continued)

*Primary Examiner* — James C. Jones
(74) *Attorney, Agent, or Firm* — Emanus, LLC; Willie Jacques (57) ABSTRACT

Systems and methods for treatment of abnormal visual development, including at least the steps of establishing determined metrics for a patient, wherein the determined metrics include at least a diameter and a distance of the patient's scotoma and/or the patient's fostoma; providing, based on the determined metrics, one or more visual therapy elements; and displaying, via an electronic device, visual representations of the one or more visual therapy elements, wherein the one or more visual therapy elements comprise visual complications and/or movements of a scotoma image and/or a fostoma image.

15 Claims, 7 Drawing Sheets

(56) References Cited

U.S. PATENT DOCUMENTS

| | | | |
|---|---|---|---|
| 9,405,135 | B2 | 8/2016 | Sweis et al. |
| 9,488,520 | B2 | 11/2016 | Howell et al. |
| 9,547,184 | B2 | 1/2017 | Howell et al. |
| 9,690,121 | B2 | 6/2017 | Howell et al. |
| 2003/0214630 | A1 | 11/2003 | Winterbotham |
| 2007/0075920 | A1 | 4/2007 | Charlesworth |
| 2008/0055541 | A1 | 3/2008 | Coulter et al. |
| 2008/0062338 | A1 | 3/2008 | Herzog et al. |
| 2008/0151175 | A1 | 6/2008 | Gross |
| 2011/0032476 | A1 | 2/2011 | Brown et al. |
| 2011/0228062 | A1 | 9/2011 | Macnaughton et al. |
| 2011/0282252 | A1 | 11/2011 | Yoo et al. |
| 2019/0385342 | A1* | 12/2019 | Freeman et al. ...... G06T 19/006 |
| 2020/0329961 | A1* | 10/2020 | Oz et al. ................... A61B 3/00 |
| 2020/0349961 | A1* | 11/2020 | Sanchez et al. ....... G10L 21/00 |

FOREIGN PATENT DOCUMENTS

| | | | |
|---|---|---|---|
| EP | 2826413 | A1 | 1/2015 |
| WO | 2003098529 | A2 | 11/2003 |
| WO | 2005043224 | | 5/2005 |
| WO | 2013165815 | A1 | 11/2013 |
| WO | 2014181270 | A1 | 11/2014 |

* cited by examiner

SYSTEMS AND METHODS FOR TREATMENT OF ABNORMAL VISUAL DEVELOPMENT

CROSS-REFERENCE TO RELATED APPLICATIONS

This patent application claims the benefit of U.S. Pat. Application Ser. No. 62/553,865, filed Sep. 3, 2017, the disclosure of which is incorporated herein in its entirety by reference.

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING COMPACT DISC APPENDIX

Not Applicable.

NOTICE OF COPYRIGHTED MATERIAL

The disclosure of this patent document contains material that is subject to copyright protection. The copyright owner has no objection to the reproduction by anyone of the patent document or the patent disclosure, as it appears in the Patent and Trademark Office patent file or records, but otherwise reserves all copyright rights whatsoever. Unless otherwise noted, all trademarks and service marks identified herein are owned by the applicant.

BACKGROUND OF THE PRESENT DISCLOSURE

1. Field of the Present Disclosure

The present disclosure relates generally to the field of treatments for abnormal visual development.

2. Description of Related Art

Amblyopia or lazy eye is a common disease of abnormal visual development affecting approximately 15 million children in the United States and over 200 million worldwide. Ambylopia develops in early childhood and results in permanent visual processing damage if not promptly and appropriately treated. This permanent damage includes loss of depth perception, developmental eye misalignment (strabismus) and loss of vision in some cases.

Depending on the disorder subtype, therapeutic options range from patching the eye with better vision (pirate's patch), ocular penalizing, pleoptics, and/or orthoptic exercises to surgical intervention to address double vision. All these options are invasive to a certain degree. The only method approved by clinical authorities is eye patching or commonly known as pirate's patch. Children up to 7 years are patched daily for 6 hours until the desired outcome is achieved. While patched, children are asked to do meaningful near activities that improve visual response such as reading, puzzles, play computer-games etc.

Any discussion of documents, acts, materials, devices, articles, or the like, which has been included in the present specification is not to be taken as an admission that any or all of these matters form part of the prior art base or were common general knowledge in the field relevant to the present disclosure as it existed before the priority date of each claim of this application.

BRIEF SUMMARY OF THE PRESENT DISCLOSURE

Unfortunately, the current treatment options are invasive and some, such as wearing a patch for an extended period, can be a challenge for children as it has the potential for creating social awkwardness and anxiety in children, thereby affecting compliance with the therapy. Furthermore, patching therapy needs to be augmented with near activities to be most effective. Limitations of patching therapy therefore mitigate its economic benefit. We have been able to modernize the patching therapy using a software algorithm that can deliver clinically mimetic therapy utilizing a smart-device.

Disclosed herein are systems and methods that provide treatment for systems and methods for treatment of abnormal visual development, such as, for example, amblyopia.

In various exemplary, non-limiting embodiments, the systems and methods of the present disclosure include at least a method that can deliver therapy utilizing a smart-device with a novel software application that is capable of simulating clinical devices.

In various exemplary, non-limiting embodiments, the systems and methods of the present disclosure include hardware solutions that are portable, user-friendly and customizable to accommodate user needs are inherently rigid. Increasing engineering costs, poor ergonomics and bulkiness of wearables renders any hardware based options cost prohibitive for the end user. A competitor's device, Amblyz™, provides therapy utilizing electronic glasses with liquid crystal displays, a product with sound scientific reasoning and clinically mimetic. The technology described herein is not a hardware solution but rather software that is capable to provide clinically mimetic therapy and easily customized to the needs of the end user.

In various exemplary, non-limiting embodiments, the core software algorithm mimics ocular occlusion therapy or eye patching, which is the only treatment method accepted by The American Academy of Pediatrics, the American Academy of Ophthalmology and the American Association of Pediatric Ophthalmology and Strabismus. The software method replicates clinical treatments that can be customized by the physician based on patient's medical needs.

In an internal focus group survey, the initial response from clinicians and parents has been encouraging because unlike a pirate's patch, the software is non-invasive, is capable of delivering appropriate therapy and can incorporate a wide range of quality assurance/quality control metrics. These metrics accurately monitor delivery and progress of treatments as well as provide seamless integration with the health care team.

In various exemplary, non-limiting embodiments, the software is comprised of a virtual layer that is displayed atop any background application.

In certain exemplary, nonlimiting embodiments, the virtual layer, may optionally comprise either a scotoma, a dark occlusion within the field of vision, or a fostoma, a light spot within the field of vision, or both.

In various exemplary, non-limiting embodiments, the software uses native elements of the electronic device operating system to generate user data, which can then be used to adjust different parameters to deliver therapy. For example, the user facing camera will be used to locate the eye movements of the end user and move the scotoma and/or the fostoma in conjunction. In some devices, therapy is delivered by electronically enhancing images. This is not the case with the software described herein, the software does not directly enhance images, rather in some embodiments creates virtual scotomas and/or virtual fostomas to deliver therapy. The software can be integrated with the healthcare electronic medical records to transfer usage and compliance reports that facilitate appropriate level of treatment.

In various exemplary, non-limiting embodiments, the systems and methods of the present disclosure utilize augmented reality components or augmented reality infrastructure to power visual treatment elements or complications.

In various exemplary, non-limiting embodiments, the methods of the present disclosure include establishing determined metrics for a patient, wherein the determined metrics comprise a diameter and a distance of the patient's scotoma and/or the patient's fostoma; and providing, based on the determined metrics, one or more visual therapy elements; and displaying, via an electronic device, visual representations of the one or more visual therapy elements, wherein the one or more visual therapy elements comprise visual complications and/or movements of a scotoma image and/or a fostoma image.

In various exemplary, non-limiting embodiments, the method further comprises determining an exposure time and a length of therapy, based on progress metrics.

In various exemplary, non-limiting embodiments, the method further comprises receiving updated metrics for the patient and altering the therapy for the patient based on the updated metrics.

In various exemplary, non-limiting embodiments, a user facing camera of the electronic device is utilized to provide the patient with feedback to ensure proper distance is maintained between the electronic device and the patient, for the duration of the therapy.

In various exemplary, non-limiting embodiments, the systems and methods of the present disclosure include an electronic device having a display; and one or more visual therapy elements displayed on the display, wherein each visual therapy element is superimposed over a background image displayed on the display of the electronic device; wherein a position of at least one of the visual therapy elements is altered within the display of the electronic device, to induce monocular or binocular movements of the patient's eye.

In various exemplary, non-limiting embodiments, each virtual therapy element is a visual ocular penalizing therapy element.

In various exemplary, non-limiting embodiments, the virtual therapy elements comprise at least one scotoma and at least one fostoma.

In various exemplary, non-limiting embodiments, the electronic device is one of a smart phone, a tablet, a tablet computer, a mobile electronic device, a portable mobile electronic device, a programmed general-purpose computer, or a special purpose computer.

In various exemplary, non-limiting embodiments, a patient facing camera of the electronic device is utilized to provide feedback to the patient, so that the display may be positioned at a determined distance from the patient's eye.

In various exemplary, non-limiting embodiments, the methods of the present disclosure include providing, on a display of an electronic device, one or more virtual therapy elements; superimposing each virtual therapy element over a background image displayed on the display of the electronic device; and altering a position of at least one of the visual therapy elements within the display of the electronic device to induce monocular or binocular movements of the patient's eye.

In various exemplary, non-limiting embodiments, the one or more virtual therapy elements comprise at least one scotoma and at least one fostoma.

In various exemplary, non-limiting embodiments, the method further comprises sizing each visual therapy element to alter the visual pathway of the background image displayed on the electronic device, as projected on a macula of the patient.

In various exemplary, non-limiting embodiments, the method further comprises providing feedback to the patient, utilizing a patient facing camera of the electronic device, so that the display may be positioned at a determined distance from the patient's eye, such that each visual therapy element is sized so as to alter the visual pathway of the background image displayed on the electronic device, as projected on a macula of the patient's eye.

In various exemplary, non-limiting embodiments, the method further comprises providing at least one central opaque spot within at least one of the virtual therapy elements.

In various exemplary, non-limiting embodiments, the method further comprises providing at least one central opaque spot, positioned centrally or eccentrically within at least one of the visual therapy elements, based on a deviation of a macula of the patient's eye.

In various exemplary, non-limiting embodiments, the method further comprises altering a position of at least one of the visual therapy elements within the display of the electronic device, so as to follow movements of the patient's eye.

In various exemplary, non-limiting embodiments, at least a portion of at least one of the visual therapy elements comprises a determined degree of transparency or translucency.

In various exemplary, non-limiting embodiments, at least one of the visual therapy elements includes a central occluding or stimulating spot, while a remaining portion of the at least one visual therapy element comprises varying degrees of transparency or translucency.

In various exemplary, non-limiting embodiments, certain edge portions of the at least one of the visual therapy elements blend into the background image displayed on the display of the electronic device.

In various exemplary, non-limiting embodiments, at least one of the visual therapy elements comprises random patterns or varying colors within determined segments of the at least one visual therapy element Accordingly, the present disclosure separately and optionally provides systems and methods that provide therapy using this modality is not invasive.

The present disclosure separately and optionally provides systems and methods that provide therapy that is highly customizable.

The present disclosure separately and optionally provides systems and methods that provide therapy that is relevant to the end user.

These and other aspects, features, and advantages of the present disclosure are described in or are apparent from the following detailed description of the exemplary, non-limiting embodiments of the present disclosure and the accompanying figures. Other aspects and features of embodiments of the present disclosure will become apparent to those of ordinary skill in the art upon reviewing the following description of specific, exemplary embodiments of the present disclosure in concert with the figures.

While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments of the systems, methods, and/or apparatuses discussed herein. In similar fashion, while exemplary embodiments may be discussed below as device, system, or method embodiments, it is to be understood that such exemplary embodiments can be implemented in various devices, systems, and methods of the present disclosure.

Any benefits, advantages, or solutions to problems that are described herein with regard to specific embodiments are not intended to be construed as a critical, required, or essential feature(s) or element(s) of the present disclosure or the claims.

BRIEF DESCRIPTION OF THE SEVERAL VIEWS OF THE DRAWINGS

As required, detailed exemplary embodiments of the present disclosure are disclosed herein; however, it is to be understood that the disclosed embodiments are merely exemplary of the present disclosure that may be embodied in various and alternative forms, within the scope of the present disclosure. The figures are not necessarily to scale; some features may be exaggerated or minimized to illustrate details of particular components. Therefore, specific structural and functional details disclosed herein are not to be interpreted as limiting, but merely as a basis for the claims and as a representative basis for teaching one skilled in the art to employ the present disclosure.

The exemplary embodiments of the present disclosure will be described in detail, with reference to the following figures, wherein like reference numerals refer to like parts throughout the several views, and wherein.

DETAILED DESCRIPTION OF EXEMPLARY EMBODIMENTS OF THE PRESENT DISCLOSURE

For simplicity and clarification, the design factors and operating principles of the systems and methods for treatment of abnormal visual development according to the present disclosure are explained with reference to various exemplary embodiments of a systems and methods according to the present disclosure. The basic explanation of the design factors and operating principles of the systems and methods for treatment of abnormal visual development is applicable for the understanding, design, and operation of the systems and methods of the present disclosure. It should be appreciated that the systems and methods can be adapted to many applications where a systems and methods can be used.

As used herein, the word "may" is meant to convey a permissive sense (i.e., meaning "having the potential to"), rather than a mandatory sense (i.e., meaning "must"). Unless stated otherwise, terms such as "first" and "second" are used to arbitrarily distinguish between the exemplary embodiments and/or elements such terms describe. Thus, these terms are not necessarily intended to indicate temporal or other prioritization of such exemplary embodiments and/or elements.

As used herein, and unless the context dictates otherwise, the terms "a" and "an" are defined as one or more unless stated otherwise.

Throughout this application, the terms "comprise" (and any form of comprise, such as "comprises" and "comprising"), "have" (and any form of have, such as "has" and "having"), "include", (and any form of include, such as "includes" and "including") and "contain" (and any form of contain, such as "contains" and "containing") are used as open-ended linking verbs. It will be understood that these terms are meant to imply the inclusion of a stated element, integer, step, or group of elements, integers, or steps, but not the exclusion of any other element, integer, step, or group of elements, integers, or steps. As a result, a system, method, or apparatus that "comprises", "has", "includes", or "contains" one or more elements possesses those one or more elements but is not limited to possessing only those one or more elements. Similarly, a method or process that "comprises", "has", "includes" or "contains" one or more operations possesses those one or more operations but is not limited to possessing only those one or more operations.

It should also be appreciated that the terms "abnormal", "abnormal visual development", "amblyopia", and "therapy" are used for basic explanation and understanding of the operation of the systems, methods, and apparatuses of the present disclosure. Therefore, the terms "abnormal", "abnormal visual development", "amblyopia", and "therapy" are not to be construed as limiting the systems, methods, and apparatuses of the present disclosure.

For simplicity and clarification, the systems and methods of the present disclosure are shown and/or described as being used in conjunction with the treatment of amblyopia. However, it should be appreciated that these are merely exemplary embodiments of the systems and methods of the present disclosure and are not to be construed as limiting the present disclosure. Thus, for example, the systems and methods of the present disclosure may be utilized as treatment methods for amblyopia or other abnormal visual developments, autism spectrum disorders, visual perceptual/visual motor deficits, dyslexia, ADHD, and non-verbal learning disabilities.

Turning now to the drawing FIGS., FIGS. 1-7 illustrate certain elements and/or aspects of an exemplary embodiment of the systems and methods for treatment of abnormal visual development, according to the present disclosure.

In illustrative, non-limiting embodiment(s) of the present disclosure, as illustrated in FIGS. 1-7, the software utilized by the systems and methods of the present disclosure is optionally configured to deliver ocular penalizing therapy to an amblyopic patient utilizing native elements of an electronic device 110. For example, software (also referred to herein as "medical device" or "apparatus") can include virtual ocular penalizing therapy elements that deliver appropriate therapy to the patient.

In certain exemplary, nonlimiting embodiments, the virtual therapy elements or visual ocular penalizing therapy elements can be overlaid over background 122 images or video displayed on the electronic device 110, while therapy is being delivered. Displaying media of the patients' choice helps to foster use and compliance by the patient.

In a departure from traditional methods and approaches, use of such software introduces quality assurance and quality control elements to therapy being delivered. Metrics such as integration with electronic medical records, usage and compliance reporting, and direct communication with the health care team can facilitate utmost level of medical care.

It should be noted that in this written description and the appended claims, the terms such as "software" and "app" are used interchangeably unless the context clearly dictates otherwise. Thus, for example, "software" is intended to mean "app" and vice versa. It should also be noted that the technology described herein is a method of delivering therapy and therefore only limited to specific software elements and not hardware. No specific attempt has been made herein to claim any prior art related to hardware elements and others including SDK (software development kit) elements, which the manufacturer has made available to software developers on a nonexclusive, nontransferable and royalty-free license in most cases. The method described herein will utilize those SDK elements provided by the manufacturer of each platform to create a method, which is claimed herein.

Figure 1:
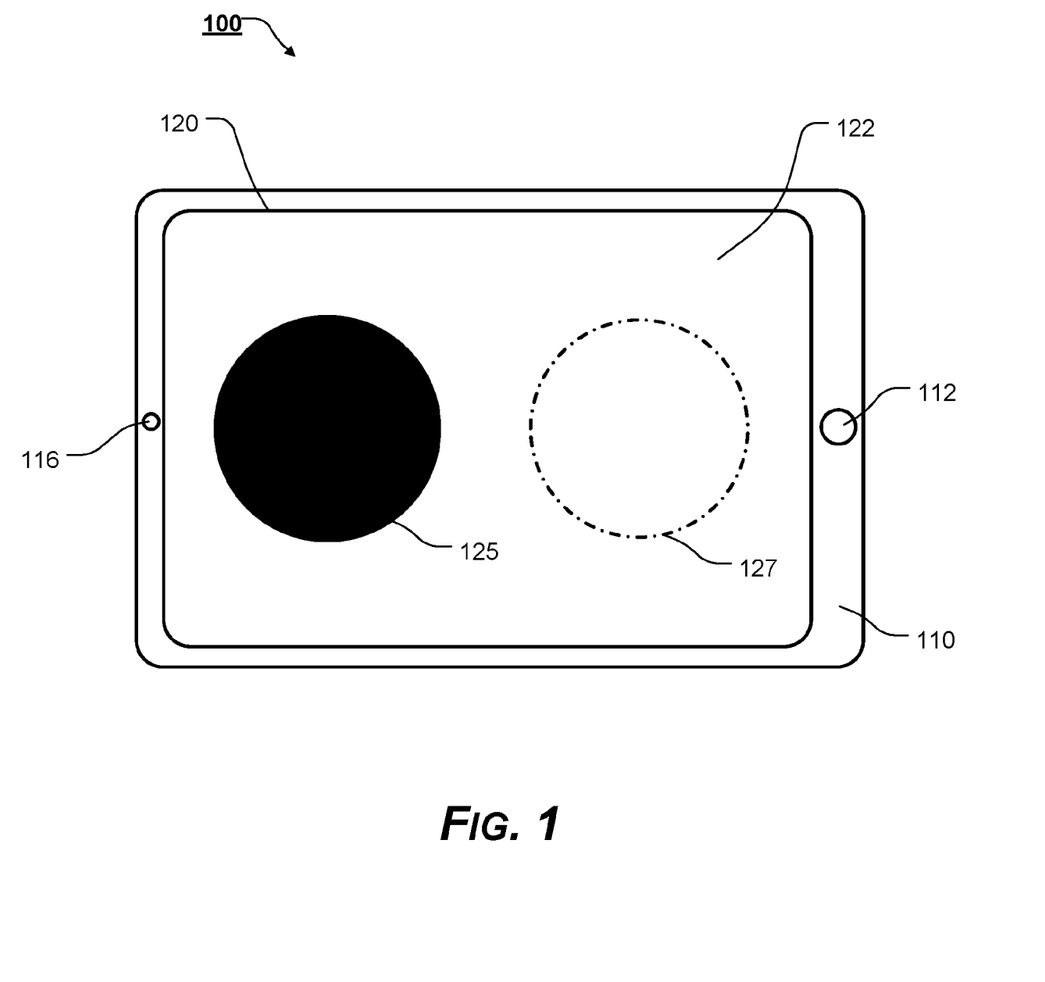
FIG. 1 illustrates an exemplary embodiment of software elements that comprise a method of delivering therapy, according to an exemplary embodiment of the present disclosure.

FIG. 1 is an illustration of an embodiment of software elements that comprise a method of delivering therapy. A method to deliver treatment utilizing software and an electronic device 110 herein referred to as electronic therapy system or e-therapy system 100 can include virtual therapy elements or visual ocular penalizing therapy elements such as a scotoma 125 and/or a fostoma 127 displayed over electronic device 110 background 122 images or video. Certain exemplary features and functions of the scotoma 125 and fostoma 127 are described herein.

In various exemplary embodiments, the electronic device 110 comprises at least some of a display 120, which may also function as a touchscreen input device, one or more cameras configured to capture video and/or still images, an audio interface comprising at least one microphone and at least one speaker, one or more device orientation sensors, such as, for example, an internal gyroscope and/or other device orientation sensors, and the requisite hardware and/or software for functional operation of the electronic device 110.

The electronic device 110 includes a memory and processing means, each electronic device 110 having a mobile device application (App) stored thereon, the App utilizing the existing audio and video capabilities of the electronic device 110.

In certain exemplary embodiments, the electronic device 110 comprises smart phone, tablet, tablet computer, mobile electronic device, portable mobile electronic device, a programmed general-purpose computer, a special purpose computer, a microprocessor, or the like.

It should be appreciated that this listing of features and/or elements included in the electronic device 110 are exemplary and not exhaustive. Thus, it should be understood that the electronic device 110, as shown and described, represents only one possible embodiment with one possible combination of features and elements. The features and elements that make up the electronic device 110 and the methods for implementing required and optional software for operation of the electronic device 110, are known in the art. Therefore, a more detailed explanation of the electronic device 110, the constituent components of the electronic device 110, instructions regarding how to incorporate the required and optional elements and/or software into the electronic device 110, methods for implementing apps and software on the electronic device 110, and certain other items and/or techniques necessary for the implementation and/or operation of the various exemplary embodiments of the presently disclosed systems and/or methods are not provided herein because such elements are commercially available and/or such background data will be known to one of ordinary skill in the art. Therefore, it is believed that the level of description provided herein with regard to the electronic device 110 and implementation of the techniques, methods, and/or apparatuses of the present disclosure is sufficient to enable one of ordinary skill in the art to understand and practice the techniques and/or methods, as described.

It should also be appreciated that the systems and/or methods disclosed herein may be implemented as software executing on a smart phone, tablet, tablet computer, mobile electronic device, portable mobile electronic device, a programmed general-purpose computer, a special purpose computer, a microprocessor, or the like. In various exemplary embodiments, the systems and/or methods disclosed herein may be implemented as an app residing in the electronic device 110, a routine embedded in a network client, as a resource residing on a network server, or the like. The systems and/or methods disclosed herein may also be implemented by incorporation into a software and/or hardware system, such as the hardware or firmware systems of the electronic device 110, or the like. In general, any device, capable of implementing the systems and/or methods disclosed herein and that is, in turn, capable of implementing the steps outlined herein, can be used as the electronic device 110, to implement the systems and/or methods disclosed herein.

The electronic device 110 can be of the end users' choice. In certain exemplary, nonlimiting embodiments, the e-therapy system 100 optionally utilizes a user facing camera 116 and/or a home button 112. The e-therapy system 100 can be available in a number of widely available platforms, such as, for example, Apple iOS™, Android™, Linux™, Java™, HTML5™, Adobe Flash ™ and Microsoft™ PowerPoint™.

It should be appreciated that these are merely exemplary embodiments of the electronic device 110 and/or platforms for utilizing the e-therapy system 100. Various examples of the different embodiments of the various components are mentioned in the following examples. It is important to note that these embodiments are only examples and many other configurations and uses of the devices described herein are contemplated.

Figure 2:
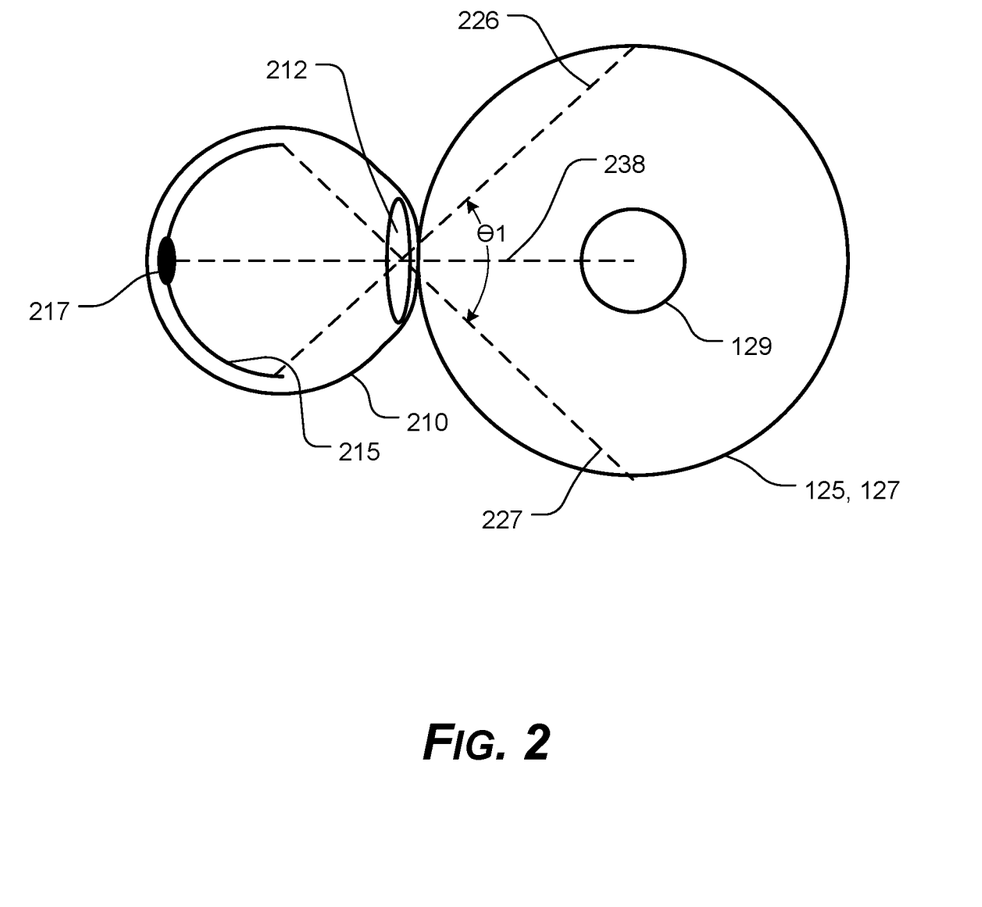
FIG. 2 illustrates an exemplary embodiment of a diameter of the therapy elements and the distance of the end user away from the display screen, according to an exemplary embodiment of the present disclosure.

FIG. 2 illustrates an exemplary embodiment of the diameter of the scotoma 125 and/or the fostoma 127 and the distance of the patient's eye 210 away from the display 120. The visual pathway of the human eye 210 includes a lens 212, which projects the image on to the retina 215. The point of greatest visual acuity is called the macula 217, which is located centrally in each eye 210.

In certain exemplary, nonlimiting embodiments, the scotoma 125 or fostoma 127 optionally have the ability to alter the visual pathway of the electronic device 110 background 122 projected on the macula 217. To deliver optimal treatment, the scotoma 125 and/or fostoma 127 have to be optimally sized.

In certain exemplary, nonlimiting embodiments, the diameter and the distance of the scotoma 125 and/or fostoma 127 from the patient's eye 210 (as represented by reference line 238) can be determined by a physician using standard methods to assess visual field. To allow for optimal visualization, the angle, 81, created by the top visual reference 226 and the bottom visual reference 227 for the scotoma 125 or fostoma 127 is no more than 150 degrees and the horizontal visual reference (as illustrated in FIG. 2) is no more than 210 degrees.

In certain exemplary, nonlimiting embodiments, the point of greatest occlusion or stimulation is a central opaque spot 129 within the scotoma 125 or fostoma 127. In other embodiments, this spot 129 can either be placed centrally or can be placed eccentrically to match the deviation of the macula 217.

Figure 3:
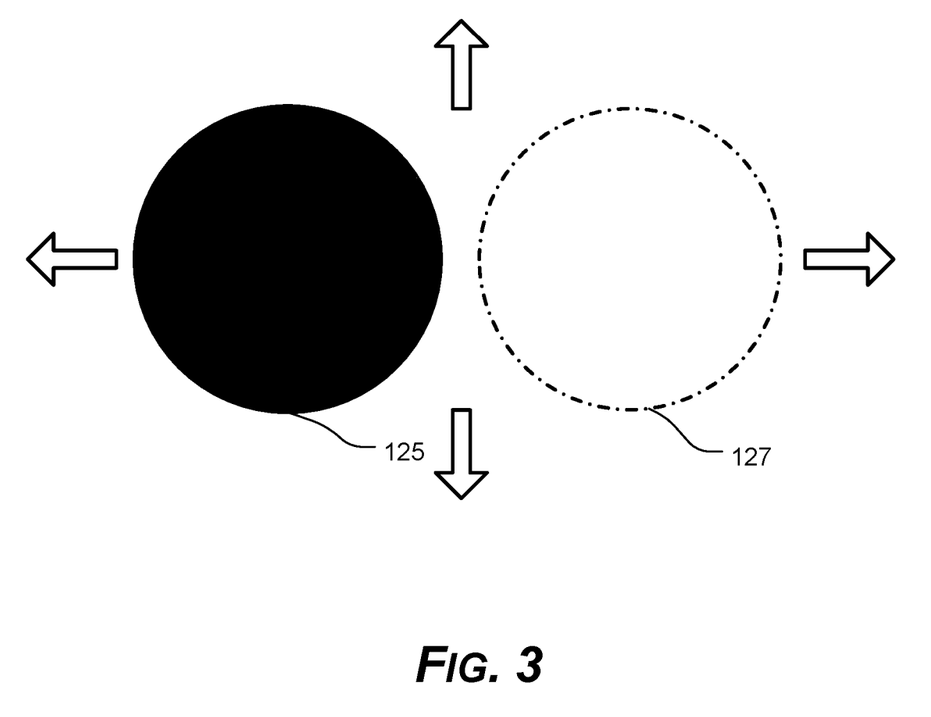
FIG. 3 illustrates an exemplary embodiment of the movement of therapy elements, according to the present disclosure.

FIG. 3 illustrates an exemplary embodiment of the movement of either the scotoma 125 and/or the fostoma 127. As in previous embodiment descriptions, the scotoma 125 and/or the fostoma 127 can appear over the electronic device 110 background 122 images or video. The scotoma 125 and/or the fostoma 127 move fluidly within the electronic device 110 environments either independently or deliberately.

In certain exemplary, nonlimiting embodiments, the movement of the scotoma 125 and/or the fostoma 127 can follow the movements of the patient's eye 210, which can be tracked by the user facing camera 116 of the electronic device 110. In other exemplary embodiments, the scotoma 125 and/or the fostoma 127 can be moved in a deliberate fashion so as to train monocular or binocular movements of the eye 210. The movements of the patient's eye 210, which are tracked by the user facing camera 116, are recorded within the e-treatment system 100, regardless of the method of movement and can be a valuable metric to the health care team to assess treatment progress.

Figure 4:
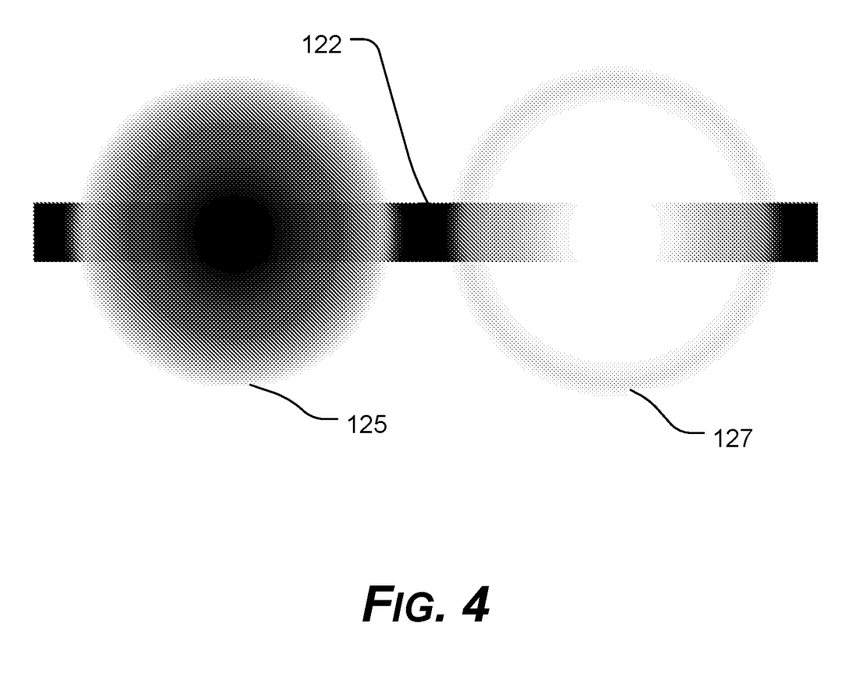
FIG. 4 illustrates an exemplary embodiment of the morphological properties of the therapy elements, according to the present disclosure

FIG. 4 is an illustration of an exemplary, nonlimiting embodiment of the morphological properties of the scotoma 125 and/or the fostoma 127. In certain exemplary, nonlimiting embodiments, the scotoma 125 and/or the fostoma 127 may optionally include a central occluding or stimulating spot 129 while the remaining portions of the scotoma 125 and/or the fostoma 127 may optionally be of varying degrees of transparency or translucency.

In certain exemplary, nonlimiting embodiments, the degree of transparency or translucency will dictate the amount of ocular penalization needed. One example of the placement of the scotoma 125 and/or the fostoma 127 appearing and occluding the electronic device 110 background 122 is illustrated in FIG. 4. In other exemplary embodiments, certain edge portions of the scotoma 125 and/or the fostoma 127 may optionally have feathered edges to seamlessly blend into the electronic device 110 background 122. As described previously, the central spot 129 may optionally be placed centrally or eccentrically within the scotoma 125 and/or the fostoma 127.

Figure 5:
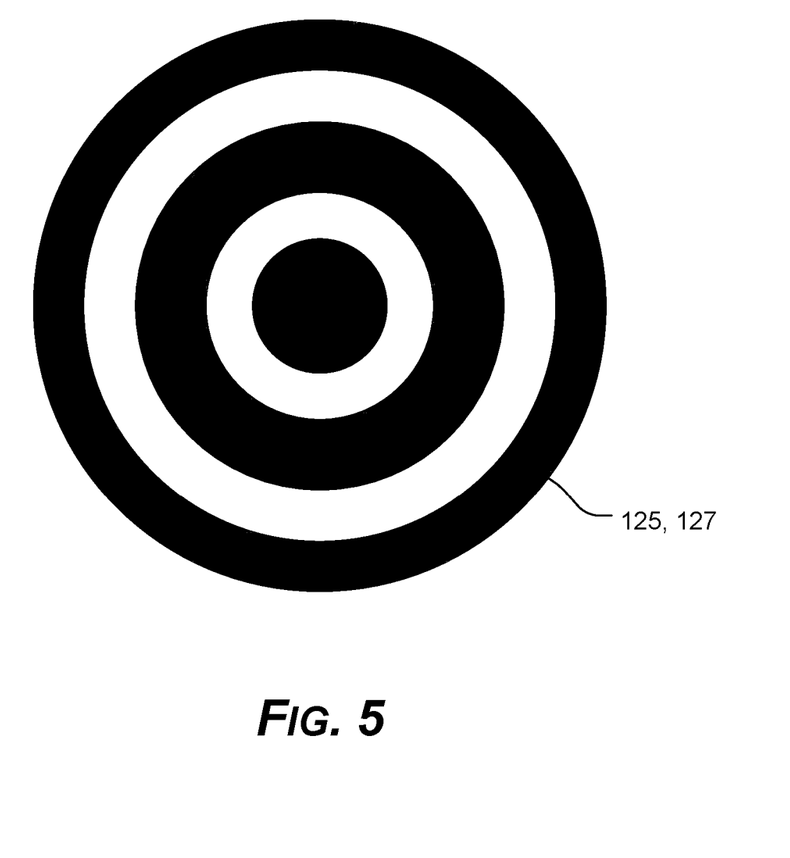
FIG. 5 illustrates an exemplary embodiment of visual elements, which can be segmented to mimic the degrees of visual field with alternate shading and/or varying levels of transparency or translucency, according to the present disclosure.
Figure 6:
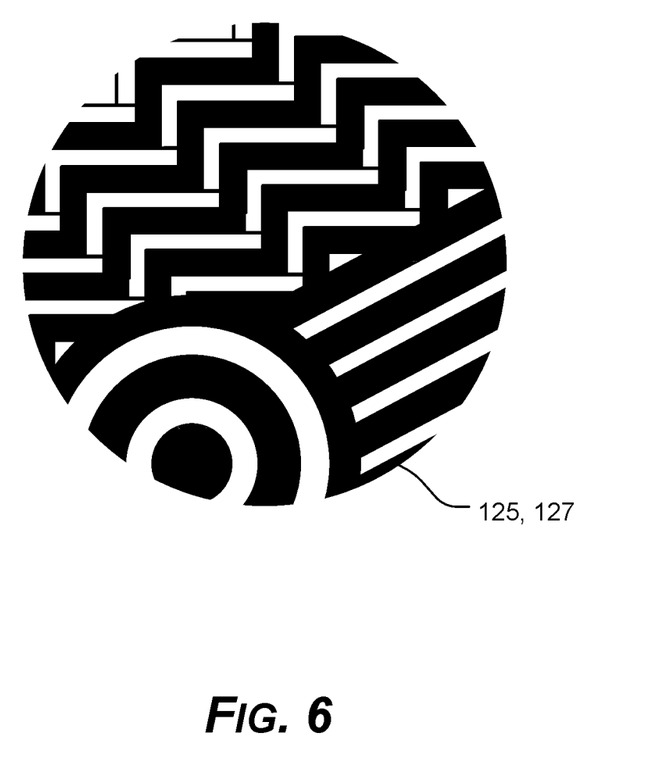
FIG. 6 illustrates an exemplary embodiment of therapy elements, which can display random patterns, random colors and in other embodiments can move in deliberate patterns to provide additional layer of therapy, according to the present disclosure.

FIGS. 5-6 illustrate different aspects of the occluding or stimulating or both elements of the e-therapy system 100. As illustrated, for example, in FIG. 5, an embodiment of the scotoma 125 and/or the fostoma 127 can possess segmentation that mimics the degrees of visual field. In other embodiments, the degree of transparency or translucency is graded over the diameter of the scotoma 125 and/or the fostoma 127. The embodiment presented in FIG. 5 displays varying colors within the segments for the scotoma 125 and/or the fostoma 127. In other embodiments of the scotoma 125 and/or the fostoma 127, FIG. 6 illustrates display of random patterns. These patterns represent visual targets, which in some embodiments can be random or deliberately placed to force meaningful ocular movements. The scotoma 125 and/or the fostoma 127 with these patterns or targets, in some embodiments, can move deliberately, randomly or along with the patient's eye movements. In certain alternate embodiments, the scotoma 125 and/or the fostoma 127 can be of varying colors that potentially could stimulate ocular photoreceptors.

Figure 7:
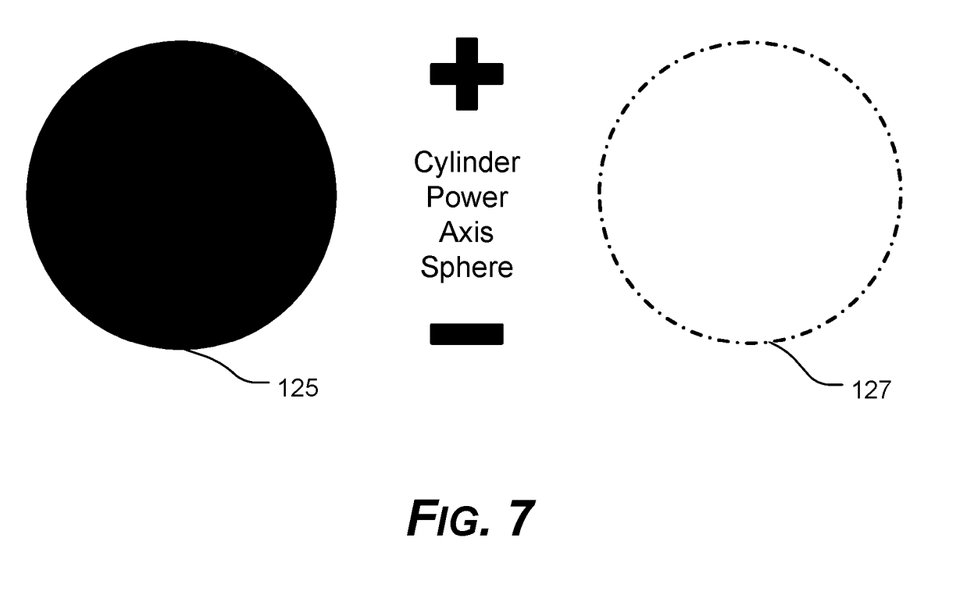
FIG. 7 illustrates an exemplary embodiment of therapy elements, which can be manipulated by the physician to correct refractive error, according to the present disclosure.

FIG. 7 illustrates an exemplary embodiment of the scotoma 125 and/or the fostoma 127, which can be manipulated by the physician to correct refractive error.

In certain exemplary, nonlimiting embodiments, the scotoma 125 and/or the fostoma 127 can be void of any visual complications, allowing for the utilization of adjustable metrics that include, but not limited to, cylinder, power, axis, and sphere to correct for refractive error.

As discussed herein, the e-therapy system 100 can be utilized to deliver ocular penalizing therapy for pediatric amblyopic patients. The therapy is delivered by virtual therapeutic elements, the scotoma 125 and/or the fostoma 127, which deliver clinically mimetic therapy. In various exemplary embodiments, the e-therapy system 100 may only be available by physician prescription and with sufficient oversight of the treatment protocol. The e-therapy system 100 may optionally provide separate dashboards for the health care team, the pediatric patient, and patient caretakers. Users in each dashboard environment have limited ability to customize individual elements. The physician retains global control of therapeutic elements.

The physician, upon initial consultation with the patient, will determine numerous metrics within the e-therapy system 100. Some examples of the metrics are described in several embodiments such as in FIG. 2, the diameter and the distance of the scotoma 125 and/or the fostoma 127 from the patient's eye (as represented by reference line 238), placement of the occluding spot 129, in FIG. 3 type of movement of the scotoma 125 and/or the fostoma 127, in FIG. 4 the degree of transparency or translucency, in FIGS. 5-6 the type of visual complications present within the scotoma 125 and/or the fostoma 127, and in FIG. 7 adjustment of the refractive error. In other embodiments, the physician can also determine the exposure time and length of therapy based on progress metrics. Additional metrics will be appended in subsequent software development cycles. The physician and the healthcare team have the ability to receive feedback from these metrics so that therapy can be delivered optimally and progress monitored. The physician and the healthcare team can modify therapeutic elements form within their dashboard environment.

It is our assumption that compliance with therapy increases when therapeutic options are relevant to the pediatric or other patient. The e-therapy system 100 delivers therapeutic elements to the patient with minimal distraction from the electronic device 110 background 122 images or video. The patient will receive therapy by way of virtual scotoma 125 and/or virtual fostoma 127, while being engrossed in relevant entertainment options playing in the electronic device 110 background 122.

In various exemplary, nonlimiting embodiments, the patient will initiate the e-therapy system 100 app on the electronic device 110, select the patient dashboard environment, and then choose the electronic device 110 background 122 image or video. The e-therapy system 100 will then reproduce therapeutic elements, as customized by the physician.

In certain exemplary, nonlimiting embodiments, patient feedback utilizing the user facing camera 116 of the electronic device 110 can help the patient ensure proper distance is maintained from the electronic device 110 for the duration of the therapy. As described in the embodiments of FIGS. 3-6, visual complications and the movements of the scotoma 125 and/or the fostoma 127 can be programmed by the physician and deployed by the e-therapy system 100 in the patient dashboard environment while receiving therapy.

In certain exemplary, nonlimiting embodiments, as illustrated, for example, in FIG. 3, tracking of the eye 210 by the user facing camera 116 can be recorded and available to the health care team.

The pediatric or other patient caretakers can utilize their portion of the dashboard environment to monitor and ensure the patient complies with the therapy provided by the e-therapy system 100. The patient caretakers can download and install the software from a platform of their choice and activate the e-therapy system 100 after physician consultation. A number of metrics can be customized from the caretaker dashboard environment.

In certain exemplary, nonlimiting embodiments, caretakers can set up reminders to initiate daily therapy, can be notified when the therapy session is over, get compliance and progress reports and interact with the health care team.

While various embodiments of the invention have been described above, it should be understood that they have been presented by way of example only, and not limitations. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

While the present disclosure has been described in conjunction with the exemplary embodiments outlined above, the foregoing description of exemplary embodiments of the present disclosure, as set forth above, are intended to be illustrative, not limiting and the fundamental disclosed systems, methods, and/or apparatuses should not be considered to be necessarily so constrained. It is evident that the present disclosure is not limited to the particular variation set forth and many alternatives, adaptations modifications, and/or variations will be apparent to those skilled in the art.

Furthermore, where a range of values is provided, it is understood that every intervening value, between the upper and lower limit of that range and any other stated or intervening value in that stated range is encompassed within the present disclosure. The upper and lower limits of these smaller ranges may independently be included in the smaller ranges and is also encompassed within the present disclosure, subject to any specifically excluded limit in the stated range. Where the stated range includes one or both of the limits, ranges excluding either or both of those included limits are also included in the present disclosure.

It is to be understood that the phraseology of terminology employed herein is for the purpose of description and not of limitation. Unless defined otherwise, all technical and scientific terms used herein have the same meaning as commonly understood by one of ordinary skill in the art to which the present disclosure belongs.

In addition, it is contemplated that any optional feature of the inventive variations described herein may be set forth and claimed independently, or in combination with any one or more of the features described herein.

Accordingly, the foregoing description of exemplary embodiments will reveal the general nature of the present disclosure, such that others may, by applying current knowledge, change, vary, modify, and/or adapt these exemplary, non-limiting embodiments for various applications without departing from the spirit and scope of the present disclosure and elements or methods similar or equivalent to those described herein can be used in practicing the present disclosure. Any and all such changes, variations, modifications, and/or adaptations should and are intended to be comprehended within the meaning and range of equivalents of the disclosed exemplary embodiments and may be substituted without departing from the true spirit and scope of the present disclosure.

Also, it is noted that as used herein and in the appended claims, the singular forms "a", "and", "said", and "the" include plural referents unless the context clearly dictates otherwise. Conversely, it is contemplated that the claims may be so-drafted to require singular elements or exclude any optional element indicated to be so here in the text or drawings. This statement is intended to serve as antecedent basis for use of such exclusive terminology as "solely", "only", and the like in connection with the recitation of claim elements or the use of a "negative" claim limitation(s).

What is claimed is:

1. A system for treatment of abnormal visual development, comprising:
    an electronic device having a display; and
    software, using a user facing camera of the electronic device, wherein said electronic device is configured to provide clinically mimetic therapy;
    one or more visual therapy elements, wherein the one or more visual therapy elements comprise visual complications and/or movements of a scotoma image and/or a fostoma image, displayed on said display, wherein each visual therapy element is superimposed over a background image displayed on said display of said electronic device; wherein a position of at least one of said visual therapy elements is altered within said display of said electronic device, to induce monocular or binocular movements of a patient's eye, wherein the one or more visual therapy elements are delivered without application of electronic glasses, to provide the clinically mimetic therapy.

2. The systems and methods of claim 1, wherein each virtual therapy element is a visual ocular penalizing therapy element.

3. The systems and methods of claim 1, wherein said virtual therapy elements comprise at least one scotoma and at least one fostoma.

4. The systems and methods of claim 1, wherein said electronic device is one of a smart phone, a tablet, a tablet computer, a mobile electronic device, a portable mobile electronic device, a programmed general-purpose computer, or a special purpose computer.

5. The systems and methods of claim 1, further comprising a patient facing camera of said electronic device, wherein said patient facing camera is utilized to provide feedback to said patient, so that said display may be positioned at a determined distance from said patient's eye.

6. A method for delivering ocular penalizing therapy to a patient, comprising:
providing, on a display of an electronic device, one or more virtual therapy elements, wherein the electronic device, including software using a user facing camera of the electronic device, provides clinically mimetic therapy;
wherein the one or more virtual therapy elements comprise at least one scotoma and at least one fostoma;
superimposing each virtual therapy element over a background image displayed on said display of said electronic device; and
altering a position of at least one of one or more visual therapy elements within said display of said electronic device to induce monocular or binocular movements of said patient's eye, wherein the one or more visual therapy elements are delivered without application of electronic glasses, to provide the clinically mimetic therapy.

7. The systems and methods of claim 6, further comprising, sizing each visual therapy element to alter said visual pathway of said background image displayed on said electronic device, as projected on a macula of said patient.

8. The systems and methods of claim 6, further comprising providing feedback to said patient, utilizing a patient facing camera of said electronic device, so that said display may be positioned at a determined distance from said patient's eye, such that each visual therapy element is sized so as to alter said visual pathway of said background image displayed on said electronic device, as projected on a macula of said patient's eye.

9. The systems and methods of claim 6, further comprising, providing at least one central opaque spot within at least one of said virtual therapy elements.

10. The systems and methods of claim 6, further comprising, providing at least one central opaque spot, positioned centrally or eccentrically within at least one of said visual therapy elements, based on a deviation of a macula of said patient's eye.

11. The systems and methods of claim 6, further comprising, altering a position of at least one of said visual therapy elements within said display of said electronic device, so as to follow movements of said patient's eye.

12. The systems and methods of claim 6, wherein at least a portion of at least one of said visual therapy elements comprises a determined degree of transparency or translucency.

13. The systems and methods of claim 6, wherein at least one of said visual therapy elements includes a central occluding or stimulating spot, while a remaining portion of said at least one visual therapy element comprises varying degrees of transparency or translucency.

14. The systems and methods of claim 6, wherein certain edge portions of said at least one of said visual therapy elements blend into said background image displayed on said display of said electronic device.

15. The systems and methods of claim 6, wherein at least one of said visual therapy elements comprises random patterns or varying colors within determined segments of said at least one visual therapy element.

\* \* \* \* \*